(12) United States Patent
Kühn et al.

(10) Patent No.: US 8,092,824 B2
(45) Date of Patent: Jan. 10, 2012

(54) ANTIBIOTIC COATING OF IMPLANTS

(75) Inventors: Klaus-Dieter Kühn, Marburg (DE); Sebastian Vogt, Erfurt (DE); Matthias Schnabelrauch, Jena (DE)

(73) Assignee: Heraeus Kulzer GmbH, Hanau (DE)

(*) Notice: Subject to any disclaimer, the term of this patent is extended or adjusted under 35 U.S.C. 154(b) by 1314 days.

(21) Appl. No.: 11/335,323

(22) Filed: Jan. 19, 2006

(65) Prior Publication Data

US 2006/0171986 A1    Aug. 3, 2006

(30) Foreign Application Priority Data

Jan. 19, 2005   (DE) .................. 10 2005 002 703

(51) Int. Cl.
   *A61F 2/02* (2006.01)
(52) U.S. Cl. ............................................... 424/425
(58) Field of Classification Search .................. None
   See application file for complete search history.

(56) References Cited

U.S. PATENT DOCUMENTS

| | | | |
|---|---|---|---|
| 3,277,003 A | 10/1966 | Gragson | |
| 3,277,033 A | 10/1966 | Gragson | |
| 3,839,297 A | 10/1974 | Wasserman et al. | |
| 4,532,929 A | 8/1985 | Mattei et al. | |
| 4,711,241 A | 12/1987 | Lehmann | |
| 4,857,602 A | 8/1989 | Casey et al. | |
| 5,032,638 A | 7/1991 | Wang et al. | |
| 5,100,433 A | 3/1992 | Bezwada et al. | |
| 5,123,912 A | 6/1992 | Kaplan et al. | |
| 5,312,437 A | 5/1994 | Hermes et al. | |
| 5,378,540 A | 1/1995 | Olson | |
| 5,607,685 A | 3/1997 | Cimbollek et al. | |
| 5,679,369 A * | 10/1997 | Brown-Skrobot | 424/431 |
| 5,736,152 A | 4/1998 | Dunn | |
| 5,888,533 A | 3/1999 | Dunn | |
| 5,968,542 A | 10/1999 | Tipton | |
| 6,303,679 B2 | 10/2001 | Schulz et al. | |
| 6,355,714 B1 | 3/2002 | Schulz et al. | |
| 6,632,457 B1 | 10/2003 | Sawhney | |
| 6,852,122 B2 | 2/2005 | Rush | |
| 2001/0000230 A1 | 4/2001 | Bernstein et al. | |
| 2004/0148010 A1 | 7/2004 | Rush | |
| 2004/0167572 A1 | 8/2004 | Roth | |

FOREIGN PATENT DOCUMENTS

| | | |
|---|---|---|
| DE | 101 14 244 A1 | 10/2002 |
| DE | 101 14 245 A1 | 10/2002 |
| DE | 101 14 364 A1 | 10/2002 |
| DE | 10114244 A1 | 10/2002 |
| DE | 102 54 215 A1 | 6/2004 |
| EP | 0 279 666 B1 | 8/1988 |
| EP | 0 328 421 B1 | 8/1989 |
| EP | 0 652 017 B1 | 5/1995 |
| EP | 0 667 161 B1 | 8/1995 |
| EP | 667161 B1 | 8/1999 |
| EP | 0 862 416 | 9/2002 |
| EP | 862416 B1 | 9/2002 |
| EP | 1 442 757 | 8/2004 |
| EP | 1442757 A | 8/2004 |
| GB | 1 090 421 | 11/1967 |
| WO | 96 39995 A1 | 12/1996 |
| WO | 9639995 A1 | 12/1996 |
| WO | WO 00/07574 | 2/2000 |
| WO | WO 00/15273 | 3/2000 |
| WO | 03/039612 | 5/2003 |
| WO | WO 03/039612 A1 | 5/2003 |
| WO | 2004 045663 | 6/2004 |

OTHER PUBLICATIONS

Rompp Chemie Lexikon, vol. 9, 1993, pp. 1343-1345.
Rompp Chemie Lexikon, vol. 9, 1993, p. 3201.
Hollemann-Wiberg "Lehrbuch der anorganischen Chemie", 101st Edition, 1995, pp. 179-212.
Rompp Chemie Lexikon, Georg Thieme Verlag, 1992, pp. 2537-2540.
Rompp Chemie Lexikon, Georg Thieme Verlag, 1992, pp. 3550-3552.
Statement of Opposition, dated Aug. 21, 2009.
In Response to the Statement of the Patent Holder by Letter of Nov. 19, 2009, dated Oct. 3, 2010.
Hollemann Wiberg, Lehrbuch der anorganischen Chemie, Walter de Gruyter, Berlin, New York 1995, 179-212.

* cited by examiner

*Primary Examiner* — Carlos A Azpuru
(74) *Attorney, Agent, or Firm* — Norris McLaughlin & Marcus PA

(57) ABSTRACT

An antibiotic coating of implants is described, which is characterized in that the coating comprises at least one saturated, organic, hydrophobic, low molecular matrix former whose melting point is in the temperature range of 45° C. to 100° C., in which a low molecular, hydrophobic additive is dissolved and that an antibiotic/antibiotics is/are suspended in the mixture of matrix former and additive and/or in which an antibiotic/antibiotics miscible with a mixture of matrix former and additive is/are dissolved.

9 Claims, No Drawings

ANTIBIOTIC COATING OF IMPLANTS

The subject matter of the invention is an antibiotic coating for implants and a process for its manufacture.

The term implant characterizes materials and devices which, in the course of a surgical intervention, are introduced at least partially into the body interior. These implants may be in contact with the bone and other elements of the framework and musculoskeletal system and also in contact with blood or connective tissue. In accident surgery and orthopaedic surgery, a wide variety of different osteosynthesis materials, endoprostheses as well as bone substitute materials are used on a large scale. However, it is a problem that, at the interface between the implant and the surrounding tissue, microbial germs may settle and cause serious infections. Infection of the bone tissue associated with the implant is one of the most serious complications when using implant material in bone tissue. The implant-associated infection requires a highly complicated and time-consuming treatment. Considerable expenditure is associated therewith. Consequently, it is appropriate to protect implant materials, especially in the first few days after implantation, which are particularly critical regarding an infection, from colonisation by germs by locally releasing antimicrobial agents at the implant surface.

Prostheses of stretched PTFE and of woven polyesters are widely used in vascular surgery to replace blood vessels. During the implantation of these vascular prostheses there is a risk that, during the period between the first few hours and days following the implantation, germs may enter the prosthesis material and colonise the inner surface of the prosthesis material. For this reason, it appears appropriate to apply a temporary antibiotic protection on the prosthesis material also in this case.

A number of antibiotic coatings based on resorbable polymers have been proposed for the protection of implant surfaces.

In EP 0 328 421, a composition is disclosed which consists of a matrix-forming polymer from the group of polyurethanes, silicones and biodegradable polymers. A synergistic combination of a silver salt with chlorhexidine is contained in these matrix formers.

In EP 0 652 017, a coating of biomaterials is presented which is to prevent blood coagulation and the adhesion of plasmic and cellular blood components to the coated biomaterial. This coating is self-adhesive on the biomaterial surface and permanently degraded in the body. The coating consists essentially of poly-a-hydroxycarboxylic acids, such as polylactic acids.

Similar technical solutions based on degradable polyesters have been disclosed in documents WO 00/15273, U.S. Pat. Nos. 3,277,003, 3,839,297, 5,378,540, 5,312,437, 5,123,912, 5,100,433, 5,032,638, 4,857,602 and 4,711,241. A problem with these coatings which contain biodegradable polymers consists of the fact that the polymer degradation takes place relatively slowly and that, in particular with coatings of implant material which are to grow into the bone tissue, a barrier effect may arise vis-a-vis the ingrowing bone tissue. The formation of acidic degradation products, such as lactic acid and glycolic acid, must also be regarded critically which are able to cause inflammatory processes in the case of a local build-up. A further problem in the case of polymeric coatings may consist of the fact that, under shear stress such as that typically occurring in the case of press-fit techniques, the entire coating may be pulled or rolled off in the form of a film.

In EP 0 279 666, a coating of surgical threads is described. This coating consists of sucrose fatty acid ester.

In U.S. Pat. No. 4,532,929, a dry coating of surgical threads is described, which is based on the use of alkaline earth fatty acid salts. Their main effect is to be that of a sizing agent.

In WO 0007574, a non-degradable medical product is proposed which comprises a substance A and a substance B, substance A being more lipophilic than substance B and substance A being more water-soluble than substance B. Substances A and B are preferably pharmaceutical active principles. It is also preferred that non-ionic surfactants are preferred as substance A.

The task of the invention consists of developing a temporary antibiotic implant coating which is applied in a cost-effective, economically advantageous manner onto a wide variety of different implant materials. This coating should be such that, on the one hand, effective quantities of antibiotics can be liberated locally at the interface between the implant and the tissue and that, on the other hand, the coating can be degraded by the adjacent human tissue within a short period without releasing toxic or acidic decomposition products. This characteristic is particularly important in the case of endoprostheses such as e.g. the non-cemented hip endoprostheses. The in-growth of the bone tissue into the porous or roughened surface structures of the non-cemented endoprostheses must not be hindered either by a relatively long-lasting barrier effect or by toxic degradation products of the antibiotic coating so as not to inhibit an optimum functioning of the endoprostheses. A further task consists of the coating to be developed adhering to the implant surface, even after shear stress such as that frequently occurring when using implants, not being pulled or rolled off in the form of a film. The coating should be largely retained even after shear stress and guarantee an antibiotic protection.

The task has been achieved in such a way that an antibiotic coating has been developed which is characterized in that the coating comprises at least one saturated, organic, hydrophobic, low molecular, degradable matrix former whose melting point is within the temperature range of 45° C. to 100° C., in which a low molecular, hydrophobic additive is dissolved and that, in the mixture of matrix former and additive, an antibiotic/antibiotics is/are suspended and/or in which an antibiotic/antibiotics miscible with the mixture of matrix former and additive is/are dissolved.

The term "saturated" should be understood to mean compounds which do not contain double or triple bond systems. The term "low molecular" should be understood to be the characteristic of the matrix former of its molecular weight being less than 1000 g/mole. The term degradable is defined here in such a way that the degradable matrix former can be degraded by the enzymes and enzyme systems such as lipases, the enzyme systems of i3-oxidation, of glycolysis and the citric acid cycle, which are commonly present in the human or animal organism. The term "hydrophobic, low molecular additive" should be understood to mean organic, hydrophobic molecules with a molecular weight of less than 1000 g/mole, which influence the adhesion of the coating on the implant surface in the sense of an improved adhesion.

Preferably, the coating is present in the solid state of aggregation in the temperature range of 20° C. to 45° C. and can be subjected to plastic deformation by pressure forces and shear forces. Plastic deformability is a highly advantageous property of the coating. As a result, it is out of the question that sharp-edged chips or particles which may possibly cause mechanical irritation, may detach themselves from the coating during implantation. In the case of a shear stress such as that arising during implantation of cement-free hip endoprostheses, in particular, the coating is deformed and presses itself into the rough surface structure of the prostheses and the surrounding spongy bone tissue.

The matrix former consists preferably of glycerine tristearate, glycerine tripalmitate, glycerine trimyristate, glycerine tribehenate, stearic acid, palmitic acid, myristic acid, behenic acid, myristyl palmitate, cetyl palmitate, ceryl cerotinate and glycerine triester, which contain different, even numbered fatty acids. The glycerine triesters represent saturated fats which adhere surprisingly well on metallic and non-metallic surfaces. In the human organism, the fats represent mainly glycerine esters of palmitic acid, stearic acid and oleic acid. In addition, small quantities of other fatty acids are contained in the fats. The matrix formers according to the invention are consequently very similar to human fat. The bone, in particular the spongy bone, contains fats itself. The fats according to the invention can be degraded without problems by the metabolic pathways for fat degradation present in the human organism. As a result, the formation of toxic or acidic degradation products such as those occurring when polylactic acids and polyglycolic acids are used, is impossible. A particular advantage consists in that the enzymatic fat degradation takes place considerably more rapidly than the hydrolytic decomposition of degradable polyesters. By using saturated glycerine triesters, the danger of the formation of decomposition products such as those arising in the case of unsaturated fats is largely avoided. The matrix former should always be applied in small quantities only, in very thin layers onto the implant surtace in order to avoid the risk of fat embolisms occurring.

Moreover, it is appropriate that the substances of the group of stearic acid, palmitic acid, myristic acid are used as low molecular, hydrophobic additive. These substances adhere very well to metal surfaces and on plastic surfaces.

It is appropriate that gentamicin sulphate, tobramycin sulphate, amikacin sulphate, netilmicin sulphate, sisomycin sulphate, vancomycin hydrochloride, teicoplanin, ramoplanin, clindamycin hydrochloride, lincomycin hydrochloride, metronidazole, tinidazole, gentamicin palmitate, gentamicin myristate, gentamicin laurate, tobramycin palmitate, tobramycin myristate, amikacin palmitate, amikacin myristate, amikacin laurate, linezolide, chlorohexidine stearate, chlorohexidine palmitate, chlorohexidine laurate, griseofulvin, nytatin, fuconazole, moxifloxazole, ciprofloxacin, fusidinic acid, rifarnpicin, rifamycin, fosfomycin, cycloserine, polyhexanide and trichlosan are preferred as antibiotics. The laurates, myristates and palmitates of the antibiotics are the fatty acid salts of the corresponding antibiotics and not the fatty acid esters of the antibiotics. The term antibiotics should be understood to mean also in a simplified manner antiseptics such as chlorohexidine, polyhexanide and trichlosan. It also corresponds to the meaning of the invention that, in addition to the antibiotics, growth factors such as BMP2 and BMP7 and hormones such as calcitonin can also be contained in the antibiotic coating. Also, it is possible that additional bisphosphonates such as zoledronate or ibandronate are integrated into the coating according to the invention. Moreover, it corresponds to the invention that the antibiotic coating is preferably formed of 1.0-98.0 percent by mass of at least one saturated, organic, hydrophobic, low molecular matrix former whose melting point is in the temperature range of 45° C. to 100° C., 0.1-5.0 percent by mass of low molecular, hydrophobic additive and 0.1-5.0 percent by weight of antibiotic/antibiotics.

The invention also relates to a process for coating in an antibiotic manner which is characterized in that a mixture of the matrix former, the additive and the antibiotic/antibiotics is heated to a temperature greater than the melting point of the matrix former and that the implant is immersed into the suspension or the homogenous melt formed, the implant having been first heated to a temperature of at least 10° C. higher than the melting point of the matrix former and that, subsequently, the coated implant is cooled to room temperature.

A process for coating in an antibiotic manner also corresponds to the invention which is characterized in that a mixture of the matrix former, the additive and the antibiotic/antibiotics is dissolved in an organic solvent and that, subsequently, the solution is sprayed onto an implant, the substrate having been heated, before spraying, to a temperature at least 10° C. higher than the melting point of the matrix former and at least 10° C. higher than the boiling point of the organic solvent and that, subsequently, the coated implant is cooled to room temperature. The process is based on the observation that mixtures of fatty acids and antibiotic fatty acid salts can be dissolved in organic solutions and these solutions can be sprayed onto surfaces. Surprisingly enough, only firmly adhering coatings are formed during this process if the implant has been first heated to a temperature at least 10° C. higher than the boiling point of the organic solvent. It has, moreover, come to light, surprisingly enough, that the mixture of fatty acids and antibiotic fatty acid salts can be partially melted and are able, during this process, to form a highly adhesive bond with a wide variety of materials. For this reason, it is appropriate that the implant to be coated has a temperature more than 10° C. higher than the melting point of the matrix former before coating.

Moreover, a process corresponds to the invention in the case of which mixtures of a matrix former, an additive and an antibiotic/antibiotics applied onto the surface of implants form, by heating to a temperature of at least the melting point of the matrix former, a coating by partial or complete melting of the mixture. Thus, it is possible, for example, to apply firmly adhering coatings of antibiotic fatty acid salts/fatty acids advantageously onto stretched PTFE prostheses.

Moreover, a process for coating in an antibiotic manner is part of the invention, which is characterized in that a mixture of the matrix former, the additive and the antibiotic/antibiotics is formed into a solid compact body and that the body is rubbed onto the surface of the implant and, as a result, a coating is separated off on the implant surface and that, optionally, the coated implant is heated to a temperature of at least the melting point of the matrix former. The body of the mixture of the matrix former, the additive and the antibiotic/antibiotics is used in a manner similar to a conventional glue pin, for example. The body is spread onto the surface to be coated. During this process, a coating is formed. This coating can be partially melted by heating to above the melting point of the matrix former. In this way, the coating receives a smoother surface and the bond between the coating and the implant surface is improved.

The invention will now be explained by the following examples without the invention, however, being restricted.

EXAMPLE 1

74.60 g of tripalmitin (a mixture of glycerine tripalmitate and glycerine tristearate) (Fluka), 0.10 g of palmitic acid (Fluka) and 25.30 g of gentamicin sulphate (AK 640) are intensively ground together. This mixture is melted at 80° C. with stirring. A milky, thin-flowing suspension is formed. A sand-blasted titanium disc (TiA16V4, d=20 mm) heated to 100° C. is immersed into this suspension. After 3 seconds, the titanium disc is removed. After cooling to room temperature, a trans-parent, waxy coating has formed. The mass of the coating is 32.5 mg (5.1 mg gentamicin base).

EXAMPLE 2

5.00 g of gentamicin pentakis palmitate (palmitic acid salt of gentamicin), 0.80 g of palmitic acid, 0.10 g of stearic acid are dissolved in 100.00 g of methanol. A see-through solution is formed. A stainless steel cylinder (d=10 mm, h=100 mm) is heated to 90° C. The methanolic solution of gentamicin palmitate/palmitic acid/stearic acid prepared previously is sprayed onto this stainless steel cylinder. A glassy, transparent, firmly adhering coating (m=88 mg) is formed with evaporation of the solvent and film formation of the mixture deposited.

EXAMPLE 3

74.60 g of tripalmitin (a mixture of glycerine tripalmitate and glycerine tristearate) (Fluka), 0.10 g of palmitic acid (Fluka) and 25.30 g of gentamicin sulphate (AK 640) are intensively ground together. This mixture is melted at 80° C. with stirring. A milky, thin-flowing suspension is formed. After cooling to room temperature, a waxy, white solid body is formed. This body is ground. The fine powder formed is applied by spraying with compressed air onto a stainless steel cylinder (d=10 mm, h=100 mm). The powder particles adhere very loosely to the metal surface. Subsequently, the metal cylinder is heated to 80° C. During this process, the powder applied melts and an even coating (m=96 mg) is formed.

EXAMPLE 4

A stainless steel cylinder (d=10 mm, h=100 mm) is heated to 80° C. and subsequently immersed for 3 seconds into a powder bed which consists of a homogenous mixture in powder form (grain size<250 pm) of 25.00 g of gentamicin pentakis palmitate (palmitic acid salt of gentamicin), 4.00 g of palmitic acid, 0.50 g of stearic acid. After removing the stainless steel cylinder from the powder bed, a layer of partially molten powder has deposited itself on the cylinder surface. The stainless steel cylinder is then heated at 80° C. for 15 minutes during which process a strongly adhering coating (m=125 mg) is formed.

EXAMPLE 5

5.00 g of gentamicin pentakis palmitate (palmitic acid salt of gentamicin), 0.80 g of palmitic acid, 0.10 g of stearic acid are dissolved in 100.00 g of methanol. A see-through solution is formed. A PTFE prosthesis (length 10 cm) is immersed into this solution. After evaporating the solvent, a thin layer (m=39.5 mg) has formed. The coated PTFE prosthesis is stored in the drying cabinet at 80° C. for 10 minutes. During this process, the coating melts partially and a homogenous, firmly adhering coating is formed.

EXAMPLE 6

5.00 g of gentamicin pentakis palmitate (palmitic acid salt of gentamicin), 0.80 g of palmitic acid, 0.10 g of stearic acid are dissolved in 100.00 g of methanol. A see-through solution is formed. A square piece of PGA felt (30 mm×30 mm) is immersed into this solution. After evaporating the solvent, a thin layer (m=35.2 mg) has formed. The coated PGA felt is stored in the drying cabinet at 80° C. for 10 minutes. During this process, the coating melts partially and a homogenous, firmly adhering coating is formed.

EXAMPLE 7

74.60 g of tripalmitin (a mixture of glycerine tripalmitate and glycerine tristearate) (Fluka), 0.10 g of palmitic acid (Fluka) and 25.30 g of gentamicin sulphate (AK 640) are intensively ground together. This mixture is melted at 80° C. with stirring. A milky, thin-flowing suspension is formed. This suspension is poured into a cylindrical mold (d=10 mm, h=10 mm). After cooling to room temperature, a white, waxy cylinder is formed. This cylinder is rubbed onto a sand-blasted titanium disc (TiA16V4, d=15 mm). A waxy, still relatively uneven coating is formed. The coated titanium disc is then stored in the drying cabinet at 80° C. for 15 minutes. During this process, partial melting takes place and an even coating is formed. The coating has a mass of 15.8 mg (2.55 mg of gentamicin base content).

What is claimed is:

1. Antibiotic coating of implants wherein the coating comprises a mixture of at least one saturated, organic, hydrophobic, low molecular matrix former selected from the group consisting of glycerine tristearate, glycerine tripalmitate, glycerine trimyristate, glycerine tribehenate, stearic acid, palmitic acid, myristic acid, behenic acid, myristyl palmitate, cetyl palmitate, ceryl cerotinate and glycerine triester, wherein each ester of said triester is formed from an even numbered fatty acid that is different from the other esters of said trimester, and whose melting point is within the temperature range of 45° C. to 100° C., in which a low molecular, hydrophobic additive selected from the group consisting of stearic acid, palmitic acid, and myristic acid is dissolved and that, in the mixture of matrix former and hydrophobic additive, at least one antibiotic is suspended and/or at least one antibiotic miscible with the mixture of matrix former and hydrophobic additive is dissolved.

2. Antibiotic coating of implants according to claim 1, wherein the coating is present in a solid state of aggregation in a temperature range of 20° C. to 45° C. and can be subjected to plastic deformation by pressure forces and shear forces.

3. Antibiotic coating of implants according to claim 1, wherein the antibiotic is one or more of gentamicin sulphate, tobramycin sulphate, amikacin sulphate, netilmicin sulphate, sisomycin sulphate, vancomycin hydrochloride, teicoplanin, ramoplanin, clindamycin hydrochloride, lincomycin hydrochloride, metronidazole, tinidazole, gentamicin palmitate, gentamicin myristate, gentamicin laurate, tobramycin palmitate, tobramycin myristate, amikacin palmitate, amikacin myristate, amikacin laurate, linezolide, chlorohexidine stearate, chlorohexidine palmitate, chlorohexidine laurate, griseofulvin, nytatin, fuconazole, moxifloxazole, ciprofloxacin, fusidinic acid, rifampicin, rifamycin, fosfomycin, cyclosérine, polyhexanide and trichlosan.

4. Antibiotic coating of implants according to claim 1, wherein the coating is formed of 1.0-98.0 percent by weight of at least one saturated, organic, hydrophobic, low molecular matrix former whose melting point is in the temperature range of 45° C. to 100° C., 0.1-5.0 percent by weight of low molecular, hydrophobic additive and 0.1-5.0 percent by weight of antibiotic/antibiotics.

5. Process for coating implants antibiotically comprising heating a composition of the matrix former, the hydrophobic additive and the at least one antibiotic according to claim 1 to a temperature greater than the melting point of the matrix former to form a suspension or a homogeneous melt and immersing the implant into the suspension or the homogenous melt formed, the implant having been first heated to a temperature at least 10° C. higher than the melting point of the matrix former and, subsequently, cooling the coated implant to room temperature.

6. Process for coating implants antibiotically comprising dissolving a mixture of the matrix former, the hydrophobic additive and the at least one antibiotic according to claim 1 in an organic solvent to form a solution and, subsequently, spraying the solution onto an implant, the implant having been heated, before spraying, to a temperature at least 10° C. higher than the melting point of the matrix former and at least 10° C. higher than the boiling point of the organic solvent and, subsequently, cooling the coated implant to room temperature.

7. Process for coating implants antibiotically comprising applying a mixture of the matrix former, the hydrophobic additive and the a least one antibiotic according to claim 1 as a layer onto an implant surface wherein the mixture applied is heated to a temperature of at least the melting point of the matrix former.

8. Process for coating implants antibiotically comprising forming a mixture of the matrix former, the hydrophobic additive and the at least one antibiotic according to claim 1 into a solid compact body, rubbing the body onto the surface of an implant and, as a result, separating off a coating on the implant surface and, optionally, heating the coated implant to a temperature of at least the melting point of the matrix former.

9. An implant coated with the coating according to claim 1.

* * * * *